United States Patent [19]

Power et al.

[11] 4,267,576

[45] May 12, 1981

[54] INTERCONNECTION SYSTEM FOR A BIOLOGICAL WAVEFORM SIMULATOR DEVICE

[75] Inventors: Joseph S. Power, Fraser; Frederick B. Ruszala, Sterling Heights, both of Mich.

[73] Assignee: The Valeron Corporation, Troy, Mich.

[21] Appl. No.: 93,086

[22] Filed: Nov. 9, 1979

[51] Int. Cl.³ .............................................. H01R 13/11
[52] U.S. Cl. .................................... 364/578; 128/695; 339/241
[58] Field of Search ................................ 364/415–417, 364/487, 578, 801; 35/17; 339/46, 241; 128/668, 695, 702

[56] References Cited

U.S. PATENT DOCUMENTS

| 3,267,934 | 8/1966 | Thornton | 128/702 |
| 3,323,068 | 5/1967 | Woods | 328/187 |
| 3,384,981 | 5/1968 | Baessler et al. | 35/17 |
| 3,552,036 | 1/1971 | Mahler | 35/17 |
| 3,736,363 | 5/1973 | Baessler et al. | 35/17 |
| 3,938,051 | 2/1976 | Eisenberg | 328/187 |

Primary Examiner—Errol A. Krass
Attorney, Agent, or Firm—Krass & Young

[57] ABSTRACT

An interconnection system for an electronic biological waveform simulator device utilized for testing the operability of a biological waveform sensing machine such as a vectorcardiogram machine. The system includes a housing with a major surface and a circuit board within the housing containing electrical circuitry for generating output signals simulating a biological waveform. A plate affixed to the major surface of the housing includes an undercut slot adapted to receive a disc-shaped electrode commonly used with the sensing machine. A connector disposed in the slot electrically connects the electrode, when engaged in the slot, with the circuitry. Preferably, the system includes a second connector projecting from an upper surface of the plate for receiving jacks utilized with disposable electrodes. In the preferred embodiment, the first and second connectors are electrically connected together so as to provide alternate signal paths for the simulated waveform from the electrical circuitry.

10 Claims, 4 Drawing Figures

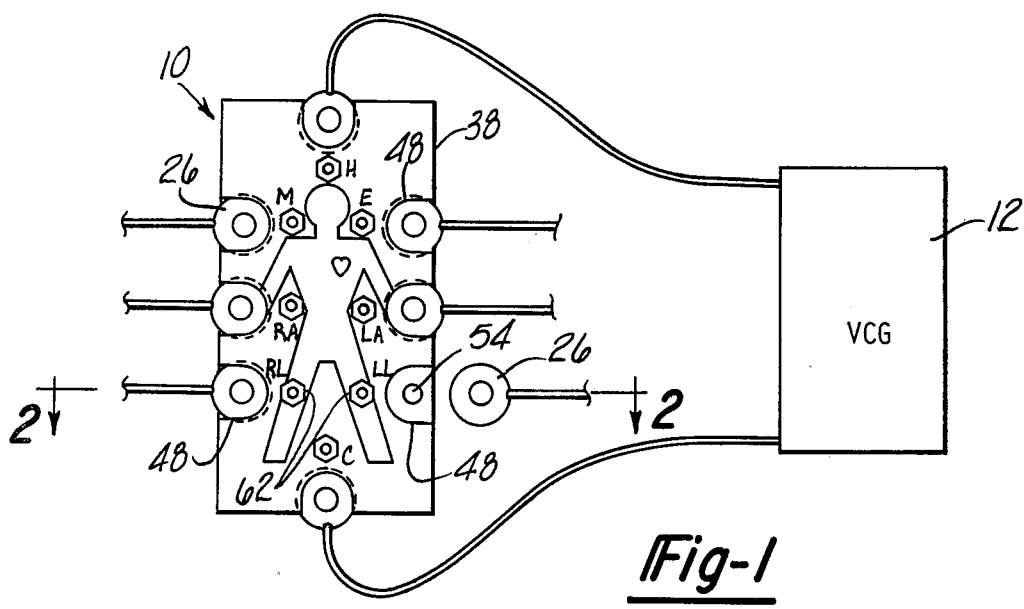
Fig-1
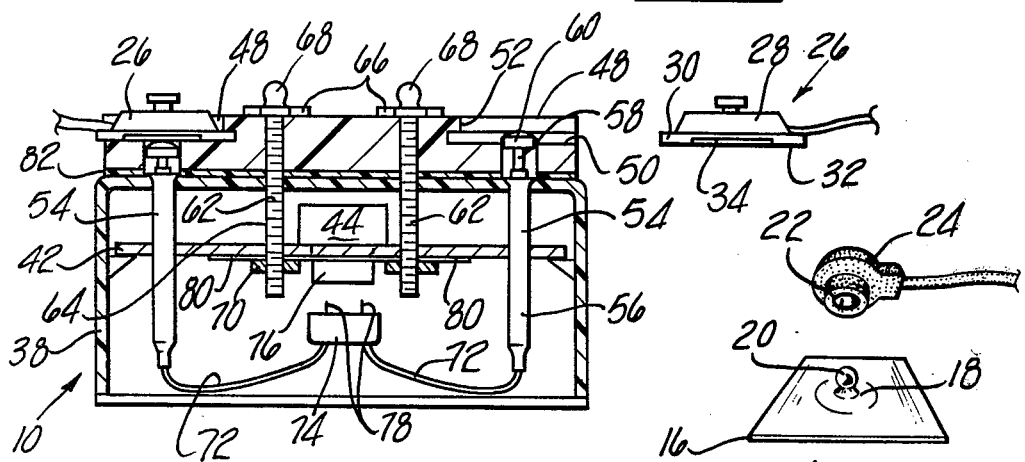
Fig-2
Fig-4
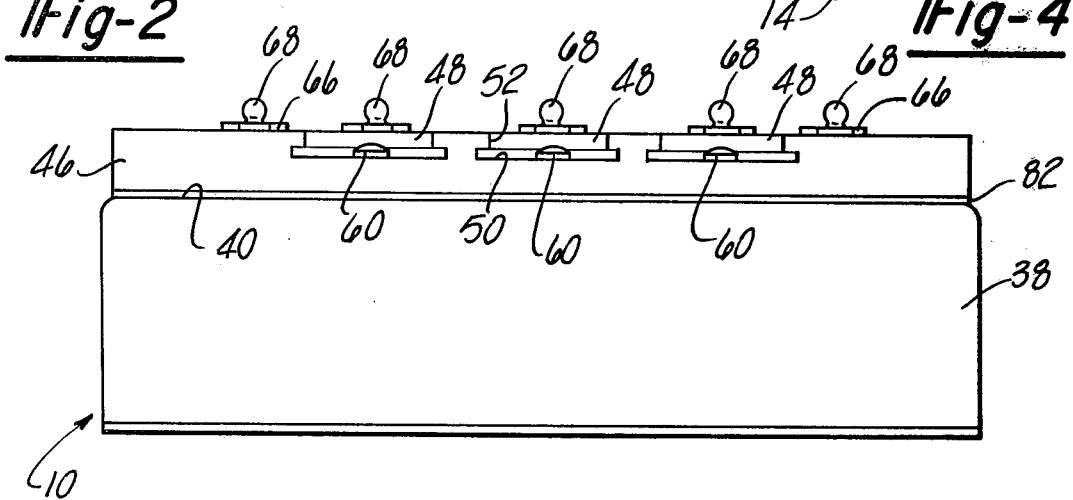
Fig-3

INTERCONNECTION SYSTEM FOR A BIOLOGICAL WAVEFORM SIMULATOR DEVICE

CROSS REFERENCE TO RELATED APPLICATION

This application is related to copending application, U.S. Ser. No. 93,085, entitled "Vectorcardiogram Simulator", filed concurrently herewith and having the same assignee as the present invention.

BACKGROUND OF THE INVENTION

This invention relates to biological waveform simulator devices. More particularly, it involves an interconnection system for such devices.

Various biological waveform simulators have been introduced into the marketplace for testing the operability of medical devices such as electrocardiogram and blood pressure monitors. Examples of such devices are disclosed and claimed in copending U.S. patent application Ser. No. 882,357, entitled "Complex Analog Signal Generator", filed Mar. 1, 1978, (now U.S. Pat. No. 4,204,261) and U.S. patent application Ser. No. 938,430, entitled "Electrocardiographic and Blood Pressure Waveform Simulator Device", filed Aug. 31, 1978, (now U.S. Pat. No. 4,205,386). These patents are hereby incorporated by reference.

These simulator devices have provided extremely satisfactory results and have enjoyed increasing popularity in the industry. In general, these devices generate substantially the same type of waveforms that would normally be supplied by a live patient or at least of sufficient quality to ascertain whether the sensing machine will work properly under normal operating conditions. The present invention is particularly concerned with an interconnection system such that the same cables and/or electrodes which are utilized for monitoring a live patient can also be plugged directly into the simulator device without further modification. This invention finds particular utility with Frank-type electrodes utilized in vectorcardiography.

SUMMARY OF THE INVENTION

The advantages and features of the present invention are accomplished by way of an interconnection system for a simulator device which includes a housing having a major surface. A circuit board within the housing contains electrical circuitry for generating an output signal simulating a biological waveform. A plate affixed to the major surface of the housing includes an undercut slot adapted to receive a disc-shaped electrode from the sensing machine. First connector means disposed in the slot electrically connect the electrode, when engaged in the slot, with the circuitry. Thus, the same electrode that is used in normal patient monitoring use may be removably inserted into the slot to couple the simulated waveforms to the sensing machine for testing its operability.

According to another feature of this invention the interconnection system includes second connector means projecting from the plate. The second connector means may be alternately used for coupling jacks utilized with disposable electrodes into the simulator. The first and second connectors are electrically connected together as to provide alternate signal paths for the output signal from the electrical circuitry.

Preferably, the plate is made of a transparent material such that an indicator card may be sandwiched between the housing and the plate for providing labels for the first and second connectors.

BRIEF DESCRIPTION OF THE DRAWINGS

These and other advantages of the present invention will become apparent upon reading the following specification and by reference to the drawings in which:

FIG. 1 is a plan view of the preferred embodiment of this invention in typical use with vectorcardiogram machine electrodes;

FIG. 2 is a cross-sectional view along the lines 2—2 of FIG. 1;

FIG. 3 is a side view of FIG. 1 without the electrodes; and

FIG. 4 is a perspective view showing a typical jack utilized with a disposable electrode.

DESCRIPTION OF THE PREFERRED EMBODIMENT

Referring now to FIG. 1, the simulator device 10 of the present invention is shown as it would be utilized in typical use with a vectorcardiogram machine 12. Vectorcardiogram machines are well known in the art. Vectorcardiography is the art of analyzing the electrical activity within the heart by obtaining electrocardiograms along three axes at right angles to one another and displaying any two of these ECG's as a vector display on an X—Y oscilloscope. Vectorcardiogram machine 12 may be such as the one manufactured by Instruments for Cardiac Research Inc. of Syracuse, N.Y.

Vectorcardiogram machines generally utilize one of two types of electrodes, the disc electrodes 26 which are shown in FIGS. 1 and 2 or the snap type disposable electrodes 14 shown in FIG. 4. The disposable electrodes 14 generally include a flexible electrically conductive pad 16. Pad 16 is electrically connected to the VCG machine 12 by way of a connector 18 having a male portion 20 which engages a corresponding female receptacle 22 in jack 24.

As shown in FIGS. 1-2, the disc-shaped electrodes 26, which are not disposable, include a bell shaped cover 28 with an upper dome and lower lip portions 30 and mouth portions 32. This disc-shaped electrode includes a circular electrically conductive contact 34 within the confines of mouth 32. VCG machine 12 generally includes eight such electrodes 26 which correspond to RA, LA, C, E, M, LL, H, and RL inputs to a Frank attenuation and compensation network within the VCG machine 12.

Simulator device 10 includes a generally rectangular housing 38 having an upper major flat surface 40. A printed circuit board 42 is mounted within housing 38 in a conventional manner. Circuit board 42 includes electrical circuitry schematically designated by the box 44 for generating an output signal simulating a biological waveform. The details of circuitry 44 are not particularly important to the present invention but it may take the form as disclosed in the above-incorporated by referenced applications or as that disclosed in copending U.S. patent application Ser. No. 93,085, entitled "Vectorcardiogram Simulator" by Schultz, Jr. et al, concurrently filed herewith and assigned to the same assignee as the present invention.

Face plate 46 is affixed to major surface 40 of housing 38. Preferably, plate 46 is made of a transparent plastic material. Plate 46 includes a plurality of undercut slots 48 spaced about its periphery. In the preferred embodiment, there are eight such slots which are specifically adapted to receive the disc shaped electrodes 26. Slots 48 each include a U-shaped bottom portion 50 which is open ended towards the periphery of plate 46. A generally conforming peripheral ledge 52 extends radially inwardly and is spaced from the bottom portion 50 a sufficient distance to permit the lip portion 30 of electrode 26 to be interposed between bottom portion 50 and the lower surface of ledge 52.

Each slot 48 includes a resilient connector 54 which projects upwardly beyond slot bottom portion 50 as can be seen most clearly in FIG. 2. Preferably, connector 54 includes an outer sleeve 56 containing a spring (not shown) in lower portions thereof which provides upward bias to piston 58. Sleeve 56 includes a flange about its upper surface for mounting onto surface 40 of housing 38. Piston 58 terminates in a rounded head 60. By inspection of FIG. 2, it can be seen that the rounded head of connector 54 permits the mouth 32 of electrode 26 to glide over head 60 while temporarily depressing it until electrode 26 is fully engaged in slot 48. When so engaged, the upward resiliency of piston 58 presses against electrode contact 34, with the ledge 52 abutting against lip portion 30 to thereby sandwich the electrode 26 in slot 48 so that good electrical connection is made.

According to another feature of this invention, device 10 includes a second set of connectors 62. Connectors 62 take the form of a threaded shaft 64, a transverse collar 66, and a ball male projection 68 for engaging female portion 22 of disposable electrode jack 24. Shaft 64 passes through openings in circuit board 42 and is secured thereto by way of nut 70. There is one such connector 62 for each of the connectors 54. Connectors 54 and 62 are electrically connected together so as to provide alternate signal paths for the output signal from the electrical circuitry 44. The sleeves 56 of connectors 54 pass through cutaway portions in the periphery of circuit board 42. The bottom portion of sleeves 56 are coupled by way of wires 72 in a ribbon cable to a dual in line package (DIP) male header or connector block 74. In FIG. 2, connector block 74 is shown disengaged with a female connector block 76. When engaged, connector blocks 74 and 76 provide an interconnection system by which electrical output signals from electrical circuitry 44 are coupled to connectors 54, the electrical circuitry 44 being connected to female receptacles (not shown) in female connector block 76. Each of these receptacles or terminals are electrically connected to corresponding pairs of connectors 54 and 62. The electrical path to connectors 54 is by way of pins 78 in connector block 74 and through their respective wires 72 in the cable. The receptacles are coupled to connectors 62 by way of conductors 80 on the printed circuit board 42 which make electrical connections to shaft 64 by way of nut 70. Therefore, according to one aspect of this invention, the interconnection system provides a means by which either disposable electrode jacks 24 or disc-shaped electrodes 26 may be utilized.

A card 82 contains illustrations and printing for labeling each pair of connectors 54 and 62. Since each pair provides an alternate connection for VCG machine 12, only one label for each pair is provided. In the particular example shown in FIG. 1, connectors 62 are disposed directly inboard of their corresponding disc electrode receiving slots 48. Card 82 contains appropriate Frank lead system electrode designations. Beginning from the lower most pair of connectors shown in FIG. 1 and moving clockwise, they are labeled C, RL, RA, M, H, E, LA, and LL, respectively.

From the foregoing specification, it can now be realized that the present invention provides a unique method of providing reliable electrical contact to disc electrodes which are normally utilized in a vectorcardiogram machine. Thus, the simulator device 10 can be plugged in directly without modifying the sensing cables utilized in vectorcardiography. Moreover, it is a feature of this invention that provision is made for accepting disposable electrode jacks as well as disc electrodes. Accordingly, the simulator device becomes universally adapted to test the operability of a variety of different types of machines. It should be noted that while this invention finds particular utility in connection with a vectorcardiogram machine, it may be utilized for a wide variety of different biological waveform sensing machines utilizing an equally wide variety of disc-type electrodes.

Therefore, while this invention has been described in connected with particular examples thereof, no limitation is intended thereby except as defined in the appended claims.

The embodiments of the invention in which an exclusive property or privilege is claimed are defined as follows:

1. An interconnection system for a simulator device for testing the operability of a biological waveform sensing machine, said system comprising:
   a housing having a major surface;
   a circuit board within the housing and containing electrical circuitry for generating an output signal for testing the operability of a biological waveform sensing machine;
   a plate affixed to the major surface of the housing, said plate having an undercut slot adapted to receive a disc-shaped electrode from the machine; and
   first connector means disposed in the slot for electrically connecting said electrode when engaged in said slot with the circuitry whereby said electrode may be removably inserted into said slot to couple the output signal to said machine for testing its operability.

2. The system of claim 1 wherein said first connector means comprises a resilient conductive member protruding from the major housing surface into said slot, operative to urge said electrode against portions of said plate when engaged in the slot to thereby insure good electrical contact between the electrode and the first connector means.

3. The system of claim 2 wherein said electrode is a nondisposable electrode used in vectorcardiogram machines, said electrode having a bell shaped cover with mouth, lip and dome portions; and wherein said slot further comprises a bottom portion generally parallel with the housing major surface for seating the mouth of the electrode, and a U-shaped peripheral ledge extending radially inwardly and spaced from the bottom portion, operative to abut the lip of the electrode while unobstructing the dome thereof, whereby said electrode may be readily slipped into the slot for making electrical connection with said first connector means.

4. The system of claim 3 wherein said first connector means comprises a spring loaded piston having a rounded head which projects through an opening in the bottom portion of the slot.

5. The system of claim 4 which further comprises:

second connector means projecting from an upper surface of said plate, operative for receiving jacks normally utilized with disposable electrodes.

6. The system of claim 5 wherein said first and second connector means are electrically connected together so as to provide alternate signal paths for the output signal from the electrical circuitry.

7. The system of claim 6 wherein said plate is made of transparent material, and wherein said system further includes a card sandwiched between the housing surface and the plate for providing labels for the connectors.

8. The system of claim 7 which further comprises: a plurality of said first connector means, operative for receiving RL, LA, C, E, M, LL, H and RL Frank system electrodes.

9. The system of claim 8 wherein said circuit board includes cutaway portions through which sleeve portions of said first connector means pass, said circuit board including a connector block having a plurality of terminals coupled to said circuitry for receiving output signals therefrom; and said sleeve portions being connected to respective ones of said terminals by way of wires in a cable.

10. The system of claim 9 wherein said second connector means includes a shaft portion which is coupled to conductors on the circuit board, said conductors being coupled to appropriate terminals in the connector block to thereby connect corresponding first and second connector means together.

* * * * *